(12) United States Patent
Packer et al.

(10) Patent No.: US 6,235,772 B1
(45) Date of Patent: May 22, 2001

(54) LIPOIC ACID ANALOGS

(75) Inventors: Lester Packer; Oren Tirosh; Chandan K. Sen; Sashwati Roy, all of Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/546,497

(22) Filed: Apr. 11, 2000

Related U.S. Application Data

(62) Division of application No. 09/037,782, filed on Mar. 10, 1998, now Pat. No. 6,090,842.

(51) Int. Cl.⁷ .................... A61K 31/385; C07D 339/02
(52) U.S. Cl. .................... 514/440; 549/39; 549/35
(58) Field of Search .................... 549/39, 35; 514/440

(56) References Cited

U.S. PATENT DOCUMENTS

| | | | |
|---|---|---|---|
| 5,084,481 | 1/1992 | Ulrich et al. | 514/557 |
| 5,334,612 | 8/1994 | Kalden et al. | 514/440 |
| 5,508,275 | 4/1996 | Weithmann et al. | 514/182 |
| 5,532,269 | 7/1996 | Koltringer | 514/440 |
| 5,569,670 | 10/1996 | Weischer et al. | 514/440 |
| 5,621,117 | 4/1997 | Bethge et al. | 549/39 |
| 5,650,429 | 7/1997 | Conrad et al. | 514/440 |
| 5,693,664 | 12/1997 | Wessel et al. | 514/440 |
| 6,013,663 * | 1/2000 | Fujita et al. | 514/440 |
| 6,090,842 * | 7/2000 | Packer et al. | 514/440 |

OTHER PUBLICATIONS

Packer et al., 1997, "α–Lipoic Acid: A Metabolic Antioxidant and Potential Redox Modulator of Transcription," *Advances in Pharmacology* vol. 38, 79–101.

Sen and Packer, 1996, "Antioxidant and redox regulation of gene transcription," *The FASEB Journal*, vol. 10, 709–720.

* cited by examiner

*Primary Examiner*—Deborah C. Lambkin
(74) *Attorney, Agent, or Firm*—Fish & Richardson P.C.

(57) ABSTRACT

A compound is provided having the formula I:

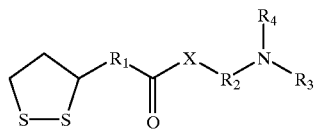

as defined in the specification. Methods of making the compounds, compositions including the compounds and methods of treatment of conditions involving reactive oxygen species are also provided.

15 Claims, 5 Drawing Sheets

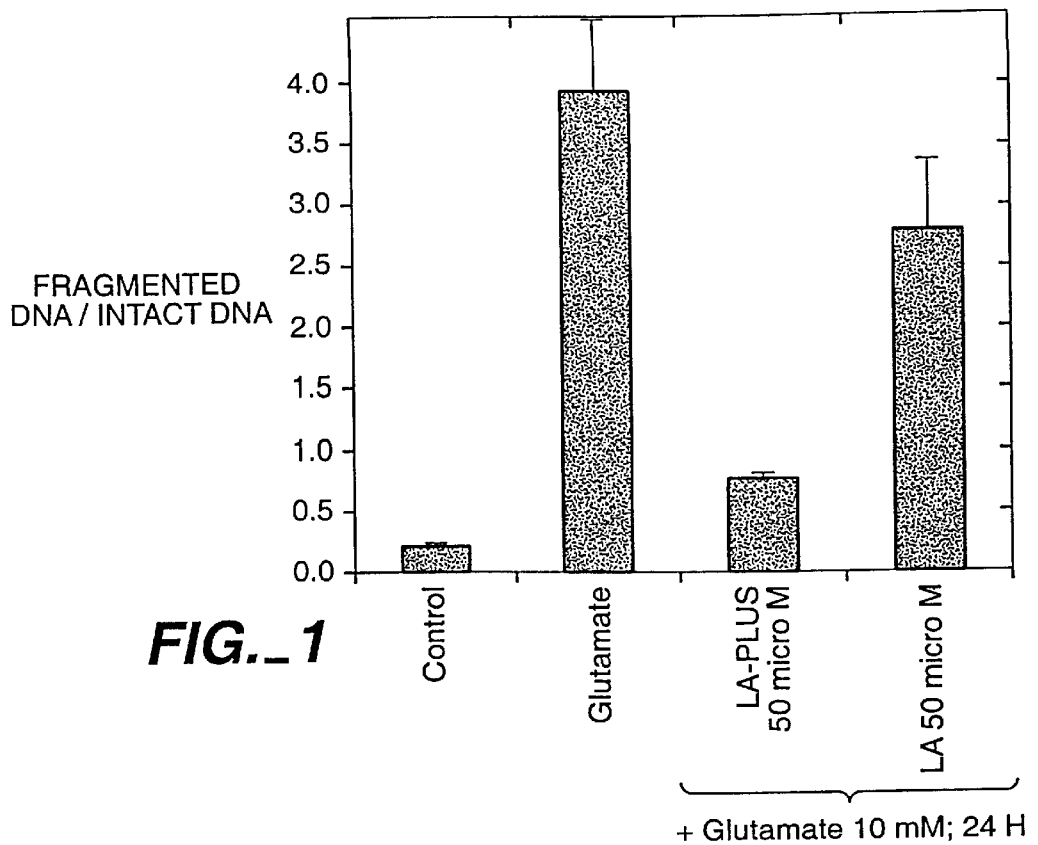
FIG._1
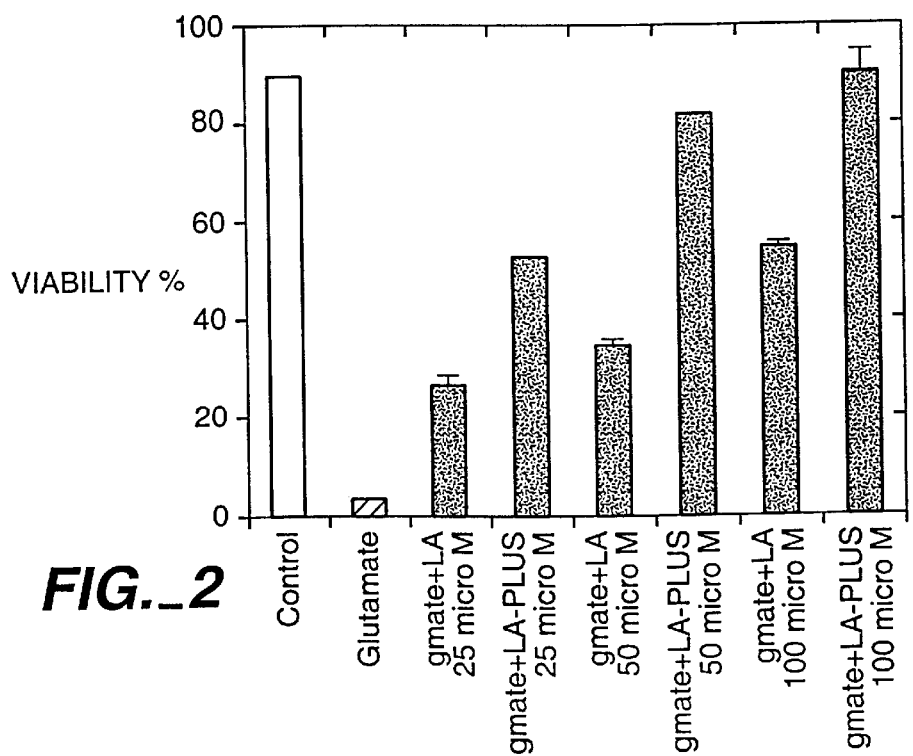
FIG._2

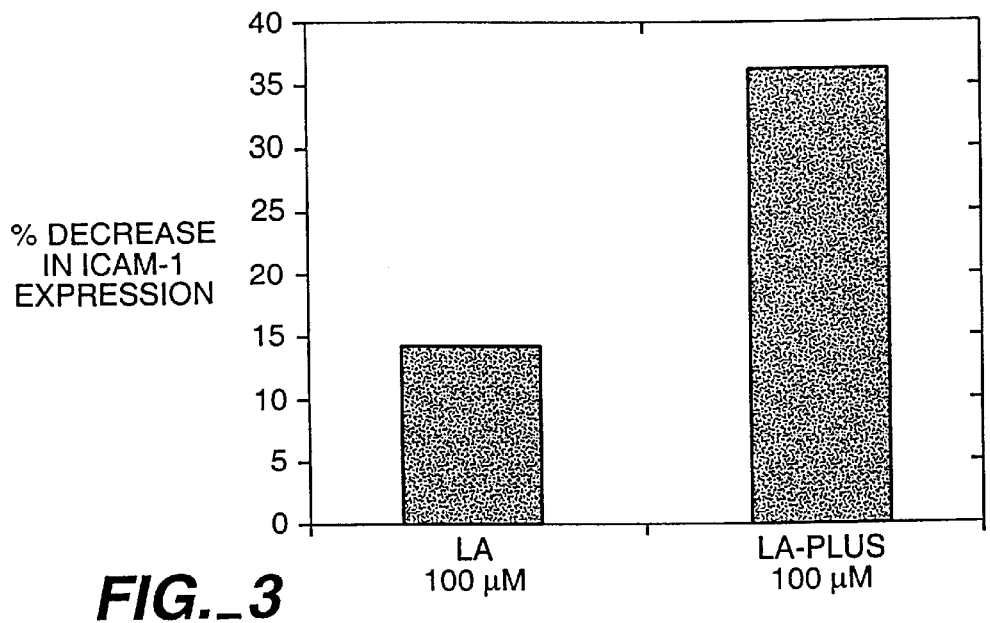
FIG._3
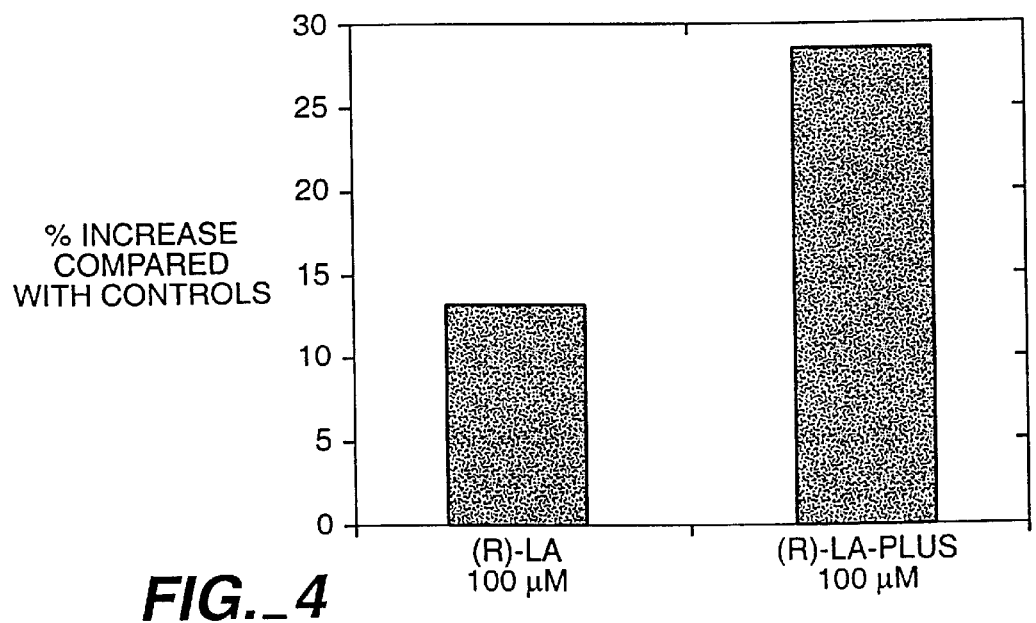
FIG._4

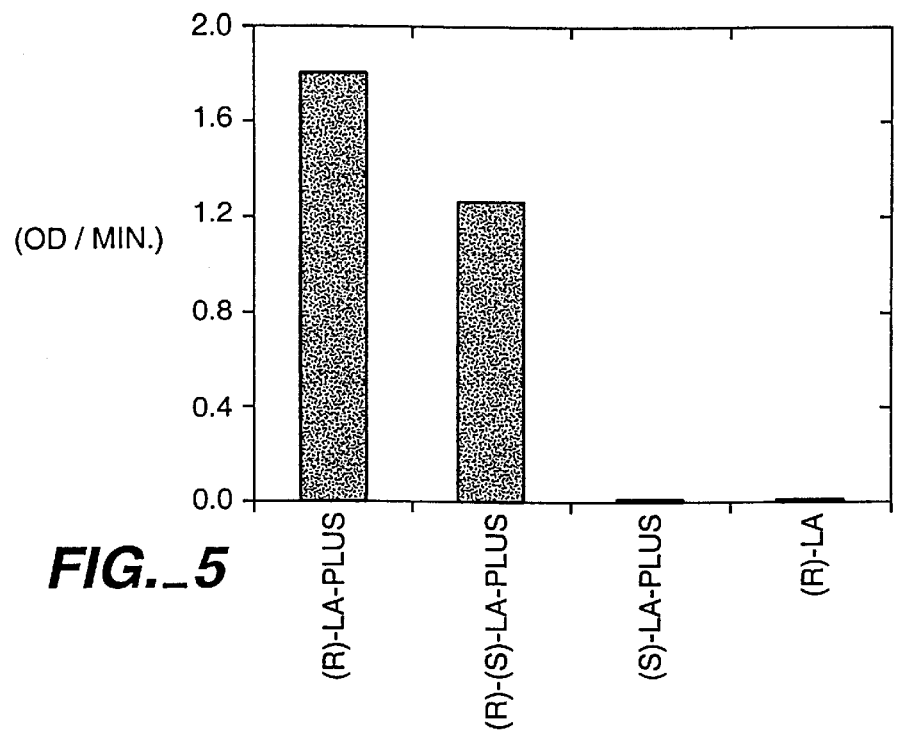
FIG._5
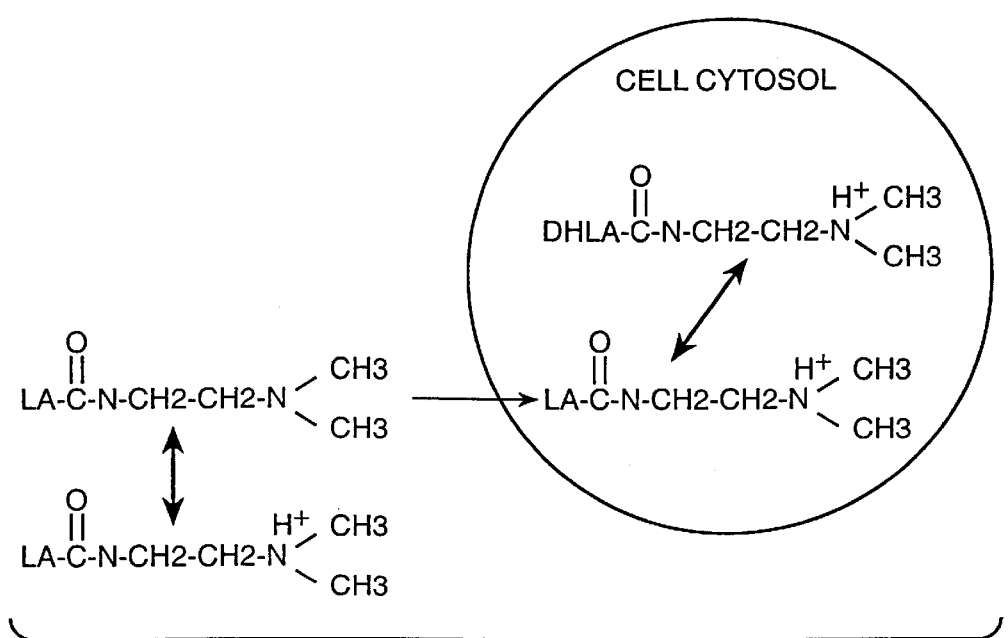
FIG._7

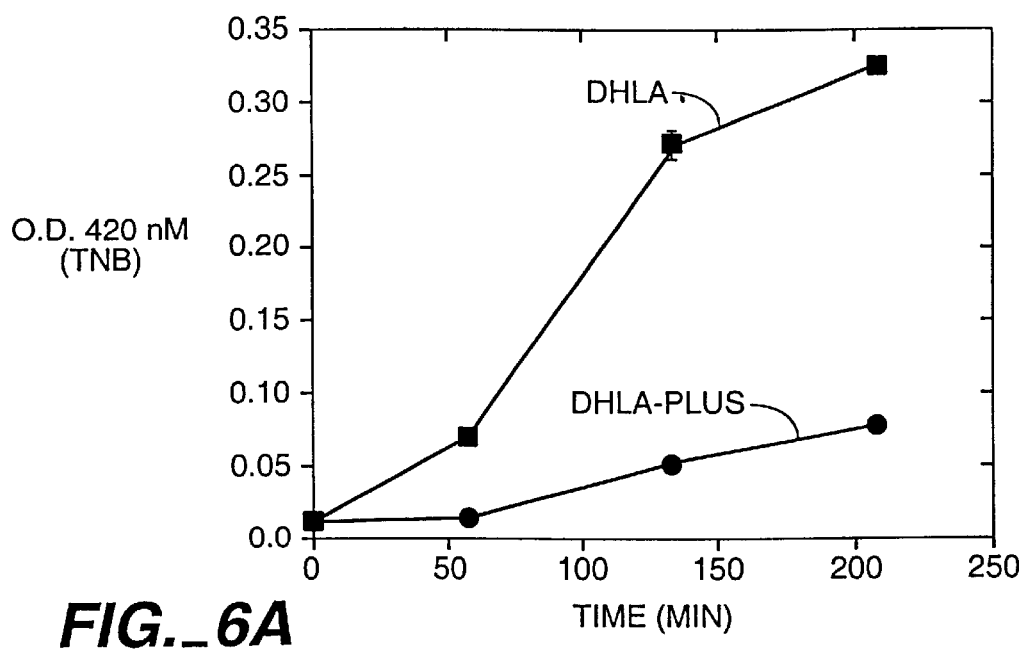
FIG._6A
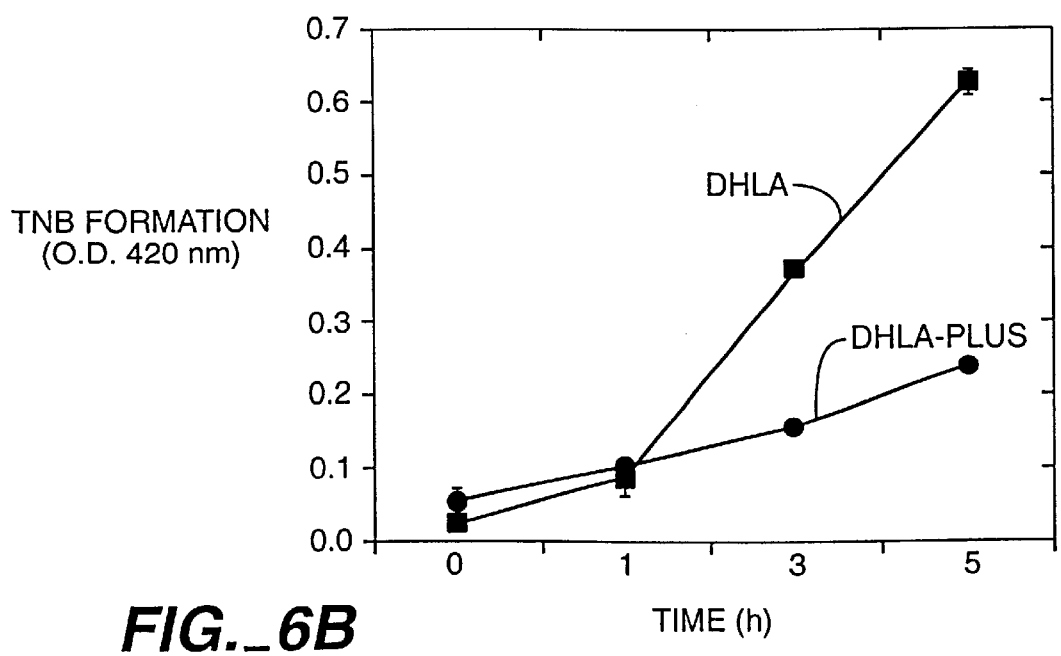
FIG._6B

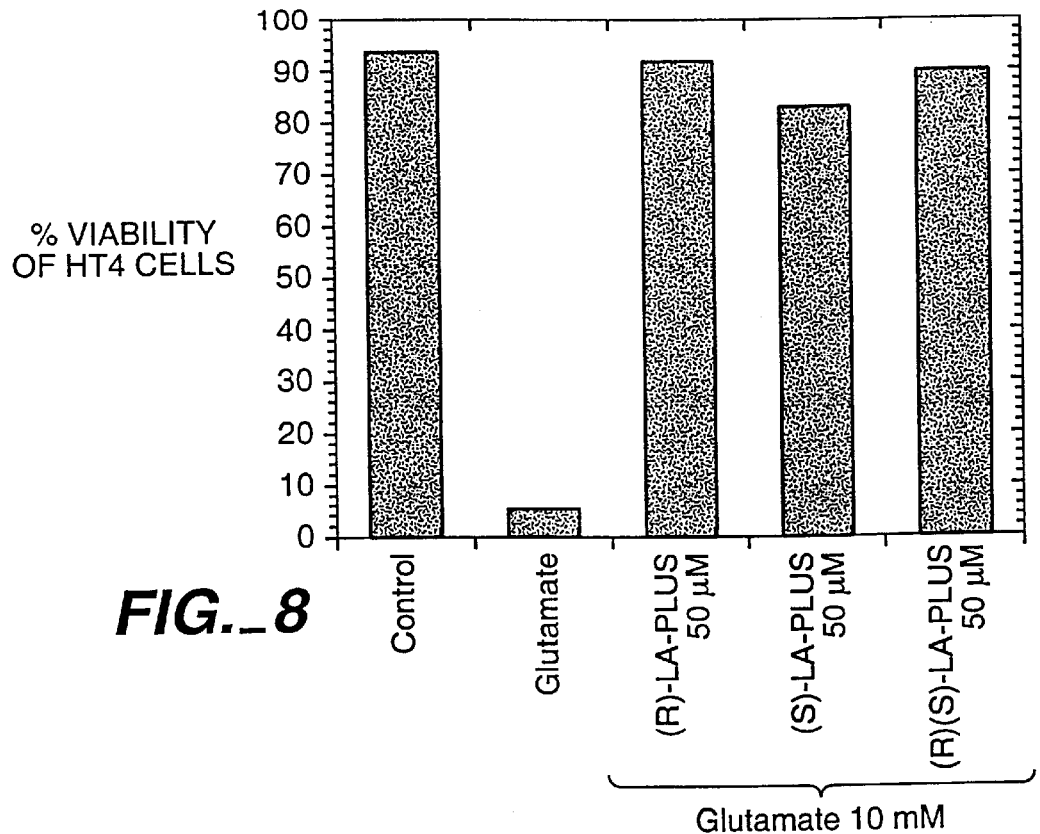
FIG._8
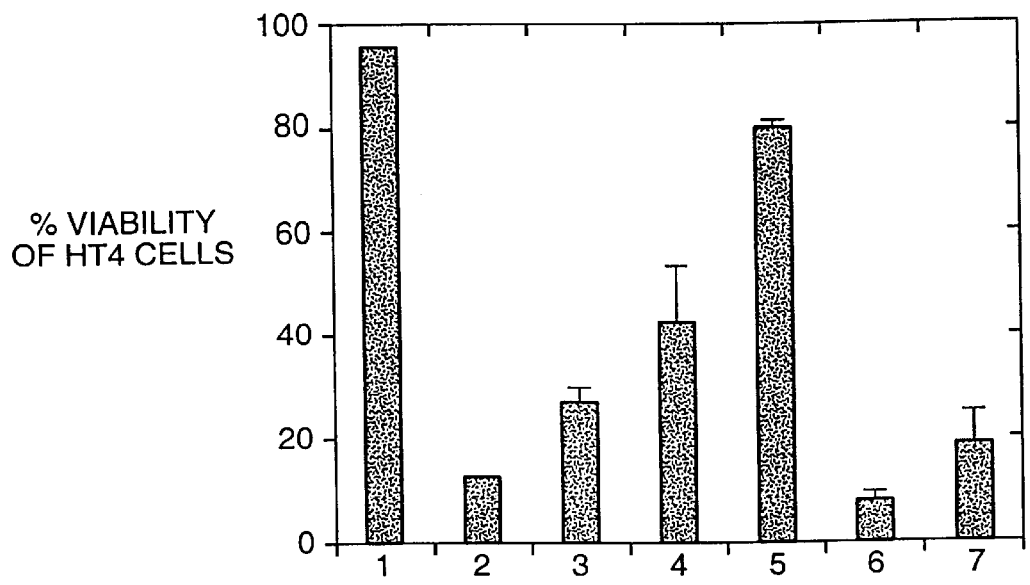
FIG._9

LIPOIC ACID ANALOGS

This patent application is a divisional of patent application Ser. No. 09/037,782, filed Mar. 10, 1998, is now U.S. Pat. No. 6,090,842 the specification of which is hereby incorporated by reference in its entirety.

This invention was made with Government support awarded by the National Institutes of Health. The Government has certain rights to this invention.

FIELD OF THE INVENTION

The present invention relates to analogs of lipoic acid, in particular lipoic acid analogs that are positively charged.

BACKGROUND OF THE INVENTION

Throughout the evolution of life on Earth, the level of oxygen in the atmosphere increased. As a result, aerobic organisms had to develop efficient defense mechanisms in order to cope with increasing oxidative stress. The toxicity of oxygen is known to be due to the formation of reactive oxygen species (ROS) during the normal metabolism of a living organism. ROS include oxygen-derived free radicals and non-radical derivatives that are capable of inciting oxidative damage to biological structures. ROS have also been shown to be involved in more than one hundred different pathological syndromes and in the aging process.

There are several lines of defense against oxidative stress, including (i) macromolecules, such as enzymes, that can interact with ROS directly and remove them, or chelate metals and prevent the augmentation of oxidative damage; (ii) low molecular weight antioxidants that can interact directly with ROS, including both synthetic antioxidants and antioxidants from natural sources; and (iii) damage repair mechanisms.

In the last five years, in addition to the conventional idea that antioxidants interact with oxidants to minimize oxidative damage, a new and exciting role of these reduction-oxidation (redox) sensitive molecules (both oxidants and antioxidants) has become clear. These molecules function in a ubiquitous redox regulation of key biological processes such as immune response, cell-cell adhesion (e.g., atherosclerosis), cell proliferation, inflammation, metabolism, glucose uptake (diabetes) and programmed cell death (apoptosis). The basic regulation mechanism is due to the existence of redox-regulated amino acids in proteins, e.g., cysteine, tyrosine and methionine. Modifications of these amino acids by either oxidants or reducing agents can trigger or inhibit the biological function of a protein.

One of the most potent naturally occurring antioxidants known is lipoic acid (LA). α-Lipoic acid is also known as thioctic acid, 1,2-dithiolane-3-pentanoic acid. 1,2-dithiolane-3-valeric acid or 6,8-thioctic acid. α-Lipoic acid has a chiral carbon atom and occurs in two enantiomeric forms.

Biologically, lipoate exists as lipoamide in at least five proteins where it is covalently linked to a lysyl residue. Four of these proteins are found in α-ketoacid dehydrogenase complexes, the pyruvate dehydrogenase complex, The branched chain keto-acid dehydrogenase complex and the α-ketoglutarate dehydrogenase complex. Three lipoamide-containing proteins are present in the E2 enzyme dihydrolipoyl acyltransferase, which is different in each of the complexes and specific for the substrate of the complex. One lipoyl residue is found in protein X, which is the same in each complex. The fifty lipoamide residue is present in the glycine cleavage system.

Recently lipoic acid has been detected in the form of lipoyllysine in various natural sources. In the plant material studied, lipoyllysine content was highest in spinach (3.15 μg/g dry weight; 92.51 μg/mg protein). When expressed as weight per dry weight of lyophilized vegetables, the abundance of naturally existing lipoate in spinach was over three- and five-fold higher than that in broccoli and tomato, respectively. Lower concentrations of lipoyllysine were also detected in garden pea, Brussels sprouts and rice bran. Lipoyllysine concentration was below detection limits in acetone powders of banana, orange peel, soybean and horseradish, however.

In animal tissues, The abundance of lipoyllysine in bovine acetone powders can be represented in the following order: kidney>heart>liver>spleen>brain>pancreas>lung. The concentration of lipoyllysine in bovine kidney and heart were 2.64±1.23 and 1.51±0.75 μg/g dry weight, respectively.

Lipoate in its reduced form as dihydrolipoate (DHLA) possesses two —SH groups which provide a very low oxidation potential to the molecule (−0.29 V). Thus, lipoic acid and the OHLA redox couple are excellent antioxidants capable of interacting with almost all forms of ROS, recycling other antioxidants and in addition reducing oxidized disulfide groups in biological systems. These molecules then may recuperate their biological reducing power and function. All of these qualities of LA make it also one of The most important molecules in redox signaling. A good example of this is the ability of this metabolically active compound to increase glucose uptake in an insulin mimic effect.

Various of the enantiomeric forms of α-lipoic acid, and combinations and derivatives thereof (including its reduced form), have been used to treat numerous conditions. For example, U.S. Pat. Nos. 5,650,429 and 5,532,269 disclose the use of lipoic acids in the treatment of circulatory disorders. U.S. Pat. No. 5,621,117 teaches that the D- and L-enantiomers of α-lipoic acid have different properties, with the D-enantiomer being primarily antiphlogistic and the L-enantiomer being mainly antinociceptive (analgesic). U.S. Pat. No. 5,569,670 discloses combinations of lipoic acids and vitamins in compositions useful for producing analgesic, anti-inflammatory, antinecrotic, anti-diabetic and other therapeutic effects. U.S. Pat. No. 5,334,612 describes certain alkylated derivatives of lipoic acid and their use in treatment of retroviral diseases. U.S. Pat. No. 5,084,481 discloses the use of reduced lipoic acid (DHLA) and salts thereof in treating inflammatory diseases. U.S. Pat. No. 6,693,664 discloses use of LA and DHLA in the treatment of diabetes. U.S. Pat. No. 5,508,275 discloses a variety of lipid-selective antioxidants, including lipoic acid derivatives.

ROS are also known to be capable of activating NF-kappa B, and it is believed that ROS are the final common signal for a number of stimuli that activate NF-kappa B. Sen and Packer, *The FASEB Journal*, Vol. 10, 709–720 (1996). The activation of NF-kappa B is believed to be involved, at least in part, in the causation or progression of a number of disease states. Packer et al., *Advances in Pharmacology*, Vol. 38, 79–101 (1997). The administration of antioxidant compositions including tocotrienyl lipoates has been proposed for regulating NF-kappa B activation in U.S. Provisional Patent Application Ser. No. 60/055,433, filed Aug. 4, 1997, which is incorporated herein in its entirety by reference.

Lipoic acid suffers from certain disadvantages, however. In particular, LA is reduced to DHLA within cells and then rapidly effluxed.

A need exists for an improved lipoic acid analog.

In addition to reactive oxygen species (ROS), reactive nitrogen species (RNS) such as nitrogen monoxide and byproducts thereof, in particular free radical byproducts thereof, have been implicated in inflammatory conditions such as diabetic neuropathy. Compositions which include lipoate derivatives, in particular tocotrienyl lipoates, have also been proposed for use in treating conditions in which RNS are involved, for example in U.S. Provisional Application Ser. No. 60/055,433.

A need exists for improved compounds that are effective in treating conditions in which RNS are involved.

SUMMARY OF THE PREFERRED EMBODIMENTS

In accordance with one aspect of the present invention, there is provided a compound having the formula I:

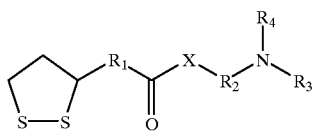

I wherein
$R^1$ and $R^2$ independently denote a methylene, ethylene or unbranched or branched $C_{3-16}$ alkylene, alkenylene or alkynylene group which is unsubstituted or substituted with one or more halogen, hydroxyl or amine groups, wherein in said unbranched or branched $C_{3-16}$ alkylene, alkenylene or alkynylene group an internal alkylene carbon atom in the carbon backbone thereof can be replaced by an oxygen atom, $R^3$ and $R^4$
  (i) independently denote
    (a) hydrogen,
    (b) a methyl, ethyl, vinyl or unbranched or branched $C_{3-16}$ alkyl, alkenyl or alkynyl group which is unsubstituted or substituted with one or more halogen, hydroxyl or amine groups, wherein in said unbranched or branched $C_{3-16}$ alkyl, alkenyl or alkynyl group an internal alkylene carbon atom in the carbon backbone thereof can be replaced by an oxygen atom,
    (c) a cycloalkyl, alkylcycloalkyl, alkenylcycloalkyl or alkynyicycloalkyl group having 5 to 16 carbon atoms which is unsubstituted or substituted with one or more halogen, hydroxyl or amine groups, or
    (d) an aryl, alkaryl, aralkyl, alkenylaryl, aralkenyl, alkynylaryl or aralkynyl group having 6 to 16 carbon atoms which is unsubstituted or substituted with one or more halogen, hydroxyl or amine groups, or
  (ii) jointly with the nitrogen atom form a cyclic or aromatic amine which is unsubstituted or substituted with one or more alkyl, alkenyl, alkynyl, halogen, hydroxyl or amine groups, X denotes O, S, —NH— or —NR$^5$—, and
R$^6$ denotes methyl, ethyl, or unbranched or branched $C_{3-16}$ alkyl,
or a pharmaceutically acceptable salt thereof, wherein said compound is in equilibrium with a protonated form thereof.

In formula 1, both the R and the S enantiomer are provided.

In a preferred embodiment, the compound is in equilibrium with a protonated form thereof at physiological pH.

In a preferred embodiment, X denotes —NH—. More particularly, $R^1$ is —(CH$_2$)$_4$—, $R^2$ is —(CH$_2$)$_2$—, and $R^3$ and $R^4$ are methyl groups or hydrogen atoms. The former particularly preferred embodiment is referred to herein as "LA-PLUS".

In another preferred embodiment, X denotes —NH—, $R^1$ is —(CH$_2$)$_4$—, $R^2$ is —(CH$_2$)$_2$—, and $R^3$ and $R^4$ form an unsubstituted or substituted pyridine or imidazole group together with the nitrogen atom.

In accordance with another aspect of the present invention, there is provided a compound having the formula II:

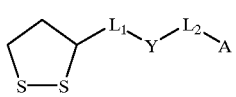

II wherein
$L^1$ and $L^2$ independently denote (i) a methylene group or a $C_{6-10}$ arylene group which is unsubstituted or substituted with a halogen, hydroxyl, amine or unbranched or branched $C_{3-16}$ alkyl, alkenyl or alkynyl group or (ii) a linking group having a carbon backbone that includes 2 to 16 carbon atoms, wherein a carbon atom in said carbon backbone can be replaced by an oxygen atom, an unsubstituted or substituted amine group, a sulfur atom, an unsubstituted or substituted $C_{6-10}$ aryl group or a combination thereof, Y denotes an ester thioester, urethane or unsubstituted or alkyl-substituted amide linkage, and A denotes a group containing a nitrogen atom that is in equilibrium with a protonated form thereof, or a pharmaceutically acceptable salt thereof. Both the R and the S enantiomers are provided.

In accordance with a further aspect of the present invention, there is provided a compound having the formula III:

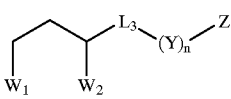

III wherein
$W^1$, $W^2$ (i) jointly denote —S—S—, —S(O)—S— or —S—S(O)—, or (ii) individually denote a group including an oxidized sulfur atom, $L^3$ denotes (i) a single bond, (ii) a methylene group or a $C_{6-10}$ arylene group which is unsubstituted or substituted with a halogen, hydroxyl, amine or unbranched or branched $C_{3-16}$ alkyl, alkenyl or alkynyl group or (iii) a linking group having a carbon backbone that includes 2 to 16 carbon atoms, wherein a carbon atom in said carbon backbone can be replaced by an oxygen atom, an unsubstituted or substituted amine group, a sulfur atom, an unsubstituted or substituted $C_{6-10}$ aryl group or a combination thereof, Y denotes an ester, thioester, urethane or unsubstituted or alkyl-substituted amide linkage, n denotes 0 or 1, and Z denotes a group containing a nitrogen atom that is in equilibrium with a protonated form thereof and increases the intracellular retention time of said compound with respect to the analogous compound having a carboxyl group, or a pharmaceutically acceptable salt thereof. Both the R and the S enantiomers are provided.

In accordance with another aspect of the present invention, methods of making the inventive compounds are provided. In a first embodiment, a method of making a compound having the formula I includes the step of reacting a compound having the formula IV

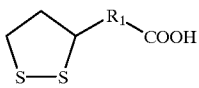

IV with a compound having the formula V $R^6—R^2—NR^3R^4$  V wherein $R^6$ denotes OH, SH, $NH_2$ or $NHR^6$.

In a second embodiment, a method of making a compound having the formula II includes the step of reacting a compound having the formula VI

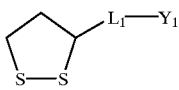

VI with a compound having the formula VII $Y^2—L^2—A$  VII wherein $Y^1$ and $Y^2$ denote groups which react to form an ester, thioester, urethane or unsubstituted or substituted amide linkage.

In a third embodiment, a method of making a compound having the formula III includes the step of reacting a compound having the formula VI

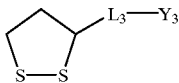

VI with a compound having the formula VIII $Y^4$  VIII to form a product, wherein $Y^3$ denotes $Y^1$ or a group that reacts with $Y^4$ to form an imine group or a guanidine group, $Y^4$ denotes $Y^2—Z$ or a reagent that reacts with $Y^3$ to form an imine group or a guanidine group, and $Y^1$ and $Y^2$ denote groups which react to form an ester, thioester, urethane or unsubstituted or substituted amide linkage, and then optionally oxidizing the product so formed.

In accordance with still another aspect of the present invention, compositions including the inventive compounds are provided. The inventive compositions include pharmaceutical compositions as well as cosmetic preparations.

In accordance with a further aspect of the present invention, methods of treating conditions in a warm-blooded animal that involve a reactive oxygen species or a redox mechanism are provided. The inventive methods include the step of administering to a warm-blooded animal having the condition an effective amount of a compound as described herein.

In preferred embodiments, the condition to be treated is a pathological condition such as diabetes, atherosclerosis, an autoimmune disease, a degenerative brain disorder such as Alzheimer's Disease, Parkinson's Disease, Huntington's Disease or epilepsy, a neoplastic disease including cancer, trauma resulting from injuries such as head injuries, cerebral ischemia, hepatic disorders, or AIDS. In another preferred embodiment, the condition is a clinical condition in which apoptosis or necrosis is implicated in pathogenesis.

In accordance with still another aspect of the present invention, methods of treating conditions in a warm-blooded animal that involve a reactive nitrogen species are provided. The inventive methods include the step of administering to a warm-blooded animal having the condition an effective amount of a compound as described herein.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which FIG. 1 is a plot showing the protection afforded against glutamate-induced apoptosis in HT4 calls by lipoic acid (LA) and an embodiment of a compound of the invention (LA-PLUS);

FIG. 2 is a plot of HT4 cell viability (LDH leakage to medium) following exposure to glutamate;

FIG. 3 is a plot showing the down-regulation of PMA-induced ICAM-1 expression by LA and LA-PLUS in human endothelial cells;

FIG. 4 is a plot showing glucose uptake in L6 rat muscle cells following treatment with LA and LA-PLUS for one hour;

FIG. 5 is a plot showing lipoamide dehydrogenase-catalyzed reduction of LA and LA-PLUS;

FIGS. 6A–B are plots showing detection of DHLA and DHLA-PLUS in the cultured medium of cells that were treated with LA or LA-PLUS, respectively, with FIG. 6A pertaining to Jurkat T cells and FIG. 6B pertaining to HT4 neuronal cells;

FIG. 7 is a plot showing entry of LA-PLUS into the cell and retention of DHLA-PLUS inside the cell;

FIG. 8 is a plot showing the protection of HT4 neuronal cells against glutamate-induced cytotoxicity afforded by R-, S- and racemic LA-PLUS; and FIG. 9 is a plot of The viability of HT4 cells following treatment with glutamate, showing the protection afforded by compounds and compositions according to the invention.

DETAILED DESCRIPTION OF THE PREFERRED EMBODIMENTS

The present invention provides analogs of lipoic acid and related compounds that have unexpectedly superior biological antioxidant capacity and redox signaling activity. This was achieved by a strategy that included converting the negative charge of the acid into a positive charge using a group that includes a moiety that is in equilibrium with a protonated form thereof at physiological pH, and therefore bears a positive charge. The inventive compounds resemble the naturally occurring form of lipoic acid, which is a conjugate between lipoic acid and the amino acid lysine. A preferred embodiment of the inventive compound (LA-PLUS) is the decarboxylation product of the naturally occurring form of lipoic acid, namely lipoyllysine (lipoyllysine itself not forming part of the present invention).

The inventive compounds can penetrate and diffuse into cells by crossing biological membranes. The compounds are then enzymatically reduced and retained inside the cell, thereby potentiating the intracellular effects thereof.

The inventive compounds are active per se, and not simply as pro-drugs for lipoic acid. The positively charged form, which is in equilibrium at physiological pH with the free base, penetrates into cells and crosses biological barriers such as membranes. Inside the cells, the compounds are enzymatically reduced and serve as powerful antioxidants.

A major drawback of LA biochemistry is that, after being taken up by cells, LA is reduced to DHLA. DHLA then is rapidly effluxed from the cell to the culture medium. Unlike LA, the inventive compounds are retained inside the cell and therefore have markedly enhanced potency compared to the effect of LA. Blocking of the terminal carboxyl group according to the invention is believed to prolong the life of the inventive compound in circulation. In blood plasma and human tissues the inventive compounds (such as LA-PLUS) are expected to have an extended biological half-life compared to the analogous acids (such as LA) because of slower beta oxidation and other metabolic processes to which unprotected acids are subjected.

Embodiments of the inventive compounds are given according to formula I:

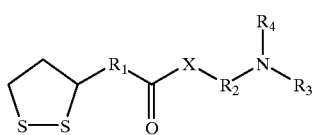

wherein
$R^1$ and $R^2$ independently denote a methylene, ethylene or unbranched or branched $C_{3-16}$ alkylene, alkenylene or alkynylene group which is unsubstituted or substituted with one or more halogen, hydroxyl or amine groups, wherein in said unbranched or branched $C_{3-16}$ alkylene, alkenylene or alkynylene group an internal alkylene carbon atom in the carbon backbone thereof can be replaced by an oxygen atom,
$R^3$ and $R^4$
(i) independently denote
  (a) hydrogen,
  (b) a methyl, ethyl, vinyl or unbranched or branched $C_{3-16}$ alkyl, alkenyl or alkynyl group which is unsubstituted or substituted with one or more halogen, hydroxyl or amine groups, wherein in said unbranched or branched $C_{3-16}$ alkyl, alkenyl or alkynyl group an internal alkylene carbon atom in the carbon backbone thereof can be replaced by an oxygen atom,
  (c) a cycloalkyl, alkylcycloalkyl, alkenylcycloalkyl or alkynyicycloalkyl group having 5 to 16 carbon atoms which is unsubstituted or substituted with one or more halogen, hydroxyl or amine groups, or
  (d) an aryl, alkaryl, aralkyl, alkenylaryl, aralkenyl, alkynylaryl or aralkynyl group having 6 to 16 carbon atoms which is unsubstituted or substituted with one or more halogen, hydroxyl or amine groups, or
(ii) jointly with the nitrogen atom form a cyclic or aromatic amine which is unsubstituted or substituted with one or more alkyl, alkenyl, alkynyl, halogen, hydroxyl or amine groups,
X denotes O, S, —NH— or —$NR^5$—, and
$R^5$ denotes methyl, ethyl, or unbranched or branched $C_{3-16}$ alkyl,
or a pharmaceutically acceptable salt thereof, wherein said compound is in equilibrium with a protonated form thereof.

Both the R and the S enantiomer are considered to be within the scope of the present invention and specifically of formula I.

In a preferred embodiment, the inventive compound is in equilibrium with the protonated form thereof at physiological pH.

Exemplary $R^1$ and $R^2$ groups include: methylene, ethylene, trimethylene, tetramethylene, pentamethylene, hexamethylene, octamethylene, decamethylene, dodecamethylene, tetradecamethylene, hexadecamethylene; propylene; chloromethylene, methylmethylene; ethylethylene, propylethylene, butylethylene; 1,1-dimethylethylene, 1,2-dimethylethylene, 1-methyl-2-ethylethylene, 1,1-diethylethylene; 1-methyltrimethylene, 2-methyltrimethylene, 3-methyltrimethylene, 1,1-dimethyltrimethylene, 1-methyl-1-ethyltrimethylene, 1,2,3-trimethyltrimethylene; 1-methyltetramethylene, 2,2-dimethyltetramethylene; 2-methylhexamethylene; 4-methyloctamethylene; 2,4-dimethyldecamethylene; vinylene; 1-propylene, 2-propylene, 1-methyl-1-propylone; 1-butenylene, 2-butenylene, 3-butenylene, 1-methyl-1-butenylene, 2-ethyl-3-butenylene; 1-pentenylene, 2-pentenylene, 4ethyl- 3-pentenylene; 1,3-butadienylene, 2-methyl-1,3-butadienylene; 1,3-pentadienylene, 2,4-pentadienylene: ethynylene; 1-propynylene, 2-propynylene, 2-methyl-1-propynylene: 1-butenylene, 2-butenylene, 3-buten-1-ynylene; chloromethylene; 1-chloroethylene, 2-fluoroethylene; 2,2-dichlorotetramethylene; 1-hydroxyethylene; 2-hydroxytrimethylene, 1,2-dihydroxytrimethylene; 1-chloro-3-hydroxyhexamethylene; 1-aminoethylene; 2,4-diaminohexamethylene; 1-methyl-3-aminotetramethylene; and the like.

Additional exemplary $R^1$ and $R^2$ groups include groups in which at least one non-terminal carbon atom in the carbon backbone of the group is replaced by an oxygen atom. Such groups include, without limitation: —$CH_2$—O—$CH_2$—; —$CH_2CH_2$—O—$CH_2$—; —$CH_2$—O—$CH_2CH_2$—; —$CH_2CH_2$—O—$CH_2CH_2$—; —$CH_2CH_2CH_2$—O—$CH_2CH_2$—, —$CH(CH_3)CH_2$—O—$CH_2CH_2$—; —$C(CH_3)_2$$CH_2$—O—$CH_2CH_2$—; —$CHClCH_2CH_2$—O—$CH_2CH_2$—, —$CH(OH)CH_2CH_2$—O—$CH_2CH_3$—; —$CH_2CH_2$—O—$CH_2CH_2$—O—$CH_2CH_2$—; —$CH_2CH_2$—O)$_3$—$CH_2CH_2$—; and the like. Such structures include ether and conjugated ether units.

If desired, $R^1$ or $R^2$ can also include a substituent that is in equilibrium with a protonated form thereof at physiological pH. Such a compound will have a positive charge of at least +2. Preferably, the inventive compound bears at most two positive charges.

Exemplary $R^3$ and $R^4$ groups include: methyl, ethyl, propyl, butyl, pentyl, hexyl, octyl, decyl, dodecyl, tetradecyl, hexadecyl; isopropyl; isobutyl, sec-butyl, tert-butyl; isopentyl, neopentyl, tert-pentyl; isohexyl; isooctyl; vinyl; allyl, 1-propenyl, isopropenyl; 1-butenyl, 2-butenyl, 3-butenyl, 1,3-butadienyl; 2-methyl-3-butenyl; 2-pentenyl; ethynyl; 2-propynyl; 4-pentynyl; chloromethyl; 1-chloroethyl, 2-fluoroethyl; 2-chloropropyl; 1,1-difluorobutyl; 2-hydroxypropyl; 1-hydroxybutyl, 2,3-dihydroxybutyl; 2-fluoro-4-hydroxyhexyl; 2-aminopropyl; 1,3-diaminohexyl; and the like.

Additional exemplary $R^3$ and $R^4$ groups include groups in which at least one non-terminal (internal) alkylene carbon atom in the carbon backbone of the group is replaced by an oxygen atom. Such groups include, without limitation: —CH$_2$—O—CH$_3$; —CH$_2$CH$_2$—O—CH$_3$; —CH$_2$—O—CH$_2$CH$_3$; —CH$_2$CH$_2$—O—CH$_2$CH$_3$; —CH$_2$CH$_2$CH$_2$—O—CH$_2$CH$_3$, —CH(CH$_3$)CH$_2$—O—CH$_2$CH$_3$; —C(CH$_3$)$_2$CH$_2$—O—CH$_2$CH$_3$; —CF$_2$CH$_2$CH$_2$—O—CH$_2$CH$_3$, —CH(NH$_2$)CH$_2$CH$_2$—O—CH$_2$CH$_3$; —CH$_2$CH$_2$—O—CH$_2$CH$_2$—O—CH$_2$CH$_3$; —(CH$_2$CH$_2$—O)$_3$—CH$_2$CH$_3$; and the like.

Unsubstituted and substituted cyclic $R^3$ and $R^4$ groups include cyclopentyl, cyclohexyl, 4-chlorocyclohexyl, 3,5-dimethylcyclohexyl, 4-tert-butylcyclohexyl, 3-cyclohexylbutyl, 4-cyclohexyl-2-butenyl, and the like. Polycyclic groups can also be used.

Unsubstituted and substituted aromatic $R^3$ and $R^4$ groups include phenyl, 4-chlorophenyl, 4-ethylphenyl, 3-phenylpropyl, 2-chloro-5-phenylpentyl, and the like. Polycyclic aromatic groups such as naphthyl, and partially aromatic polycyclic groups such as indyl, which can be further substituted with alkyl, alkenyl, alkynyl, halogen, hydroxyl or amine groups, can also be used.

Furthermore $R^3$ and $R^4$ can, together with the nitrogen atom to which they are bonded, form a cyclic or aromatic amine group, including polycyclic groups. Exemplary groups formed jointly by $R^3$, $R^4$ and N in formula I include: 1-pyridyl; 3-carboxy-1-pyridyl (nicotinic acid derivative); 1-imidazolyl; 1-indolyl; 1-piperidyl; 1-pyrazolyl; 1-benzpyrazolyl; and the like. The cyclic or aromatic amine groups can also be further substituted with one or more alkyl, alkenyl, alkynyl, halogen, hydroxyl or amine groups.

As with $R^1$ and $R^2$, the $R^3$ and $R^4$ groups can also include an additional substituent which is positively charged at physiological pH, resulting in a compound with a charge of at least +2. Again, it is preferable that the total charge of the inventive compound not exceed +2. More particularly, the charge of the inventive compound is +1 at physiological pH when it is dissociated from its counterion in solution.

Preferred embodiments include those in which X=—NH—, and more specifically those in which $R^1$ and $R^2$ are polyalkylene groups, and $R^3$ and $R^4$ are methyl groups or jointly form an unsubstituted or substituted pyridine or imidazole group together with the nitrogen atom. Particularly preferred is the "LA-PLUS" embodiment in which $R^1$ is —(CH$_2$)$_4$—, $R^2$ is —(CH$_2$)$_2$—, and $R^3$ and $R^4$ are methyl groups. In a preferred variant of LA-PLUS, $R^3$ and $R^4$ are hydrogen atoms.

More generally, compounds according to the invention are provided according to formula II:

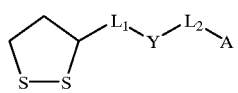

II

In formula II,
$L^1$ and $L^2$ independently denote (i) a methylene group or a $C_{6-10}$ arylene group which is unsubstituted or substituted with a halogen, hydroxyl, amine or unbranched or branched $C_{3-16}$ alkyl, alkenyl or alkynyl group or (ii) a linking group having a carbon backbone that includes 2 to 16 carbon atoms, wherein a carbon atom in said carbon backbone can be replaced by an oxygen atom, an unsubstituted or substituted amine group, a sulfur atom, an unsubstituted or substituted $C_{6-10}$ aryl group or a combination thereof, Y denotes an ester, thioester, urethane or unsubstituted or alkyl-substituted amide linkage, and A denotes a group containing a nitrogen atom that is in equilibrium with a protonated form thereof, or a pharmaceutically acceptable salt thereof.

In Formula II, A includes all groups of the form —NR$^3$R$^4$ as set forth above. Further exemplary A groups include imine groups having the formulae IIa–b:

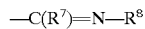     IIa

     IIb wherein
$R^7, R^8$ denote hydrogen, a methyl group, a $C_{6-10}$ aryl group which is unsubstituted or substituted with a halogen, hydroxyl, amine or unbranched or branched $C_{3-16}$ alkyl, alkenyl or alkynyl group, or an unbranched or branched $C_{2-16}$ alkyl, alkenyl or alkynyl group which is unsubstituted or substituted with a halogen, hydroxyl or amine group, and guanidine groups having the formula IIc:

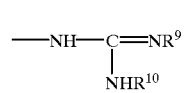     IIc wherein
$R^9$, $R^{10}$ denote hydrogen or $C_{1-6}$ alkyl.

The A group can also include additional linking groups, for example additional $L^1$ groups, and additional ester, thioester, urethane and/or amide linkages, affording a polymer-like structure of the form —Y—L—Y— . . . .

Exemplary $L^1$ and $L^2$ groups include those set forth above in connection with the $R^1$ and $R^2$ groups of formula I. Additional exemplary $L^1$ and $L^2$ groups include groups in which at least one non-terminal carbon atom in the $C_{2-16}$ carbon backbone of the group is replaced by a sulfur atom. Such groups include, without limitation: —CH$_2$—S—CH$_2$—; —CH$_2$CH$_2$—S—CH$_2$—; —CH$_2$—S—CH$_2$CH$_2$—; —CH$_2$CH$_2$—S—CH$_2$CH$_2$—; —CH$_2$CH$_2$CH$_2$—S—CH$_2$CH$_2$—, —CH(CH$_3$)CH$_2$—S—CH$_2$CH$_2$—; —C(CH$_3$)$_2$CH$_2$—S—CH$_2$CH$_2$—; —CHClCH$_2$CH$_2$—S—CH$_2$CH$_2$—, —CH(OH)CH$_2$CH$_2$—S—CH$_2$CH$_3$—; —CH$_2$CH$_2$—S—CH$_2$CH$_2$—S—CH$_2$CH$_2$—; —(CH$_2$CH$_2$—S)$_3$—CH$_2$CH$_2$—; and the like.

Further exemplary $R^1$ and $R^2$ groups include groups in which at least one carbon atom in the $C_{2-16}$ carbon backbone of the group is replaced by an unsubstituted or substituted amine group. In the latter case, the amine group preferably is substituted with an unbranched or branched $C_{3-16}$ alkyl, alkenyl or alkynyl group. Such groups include, without limitation: —CH$_2$—NH—CH$_2$—; —CH$_2$—N(CH$_3$)—CH$_2$—; —CH$_2$—N(CH$_2$CH$_3$)—CH$_2$—; —CH$_2$CH$_2$—NH—CH$_2$—; —CH$_2$—N(CH$_2$CH$_3$)—CH$_2$CH$_2$—; —CH$_2$CH$_2$—NH—CH$_2$CH$_2$—; —CH$_2$CH$_2$CH$_2$—N(CH$_2$CH$_2$CH$_3$)—CH$_2$CH$_2$—; —CH(CH$_3$)CH$_2$—NH—CH$_2$CH$_2$—; —C(CH$_3$)$_2$CH$_2$—NH—CH$_2$CH$_2$—; —CH$_2$CH$_2$CH$_2$—N(CH$_2$CH$_2$CH$_3$)—CH$_2$CH$_2$—; and the like.

Additional $L^1$ and $L^2$ groups include unsubstituted or substituted $C_{6-10}$ arylene groups, and gropus in which one or more carbon atoms in the $C_{2-16}$ carbon backbone thereof are replaced with an unsubstituted or substituted aryl group. Combinations of aryl and oxygen sulfur and/or amine groups can also be included, as well as partially aromatic polycyclic groups. Polymeric structures including repeated aryl, alkaryl, etc. units can also be included.

Exemplary $L^1$ and $L^2$ groups include without limitation:

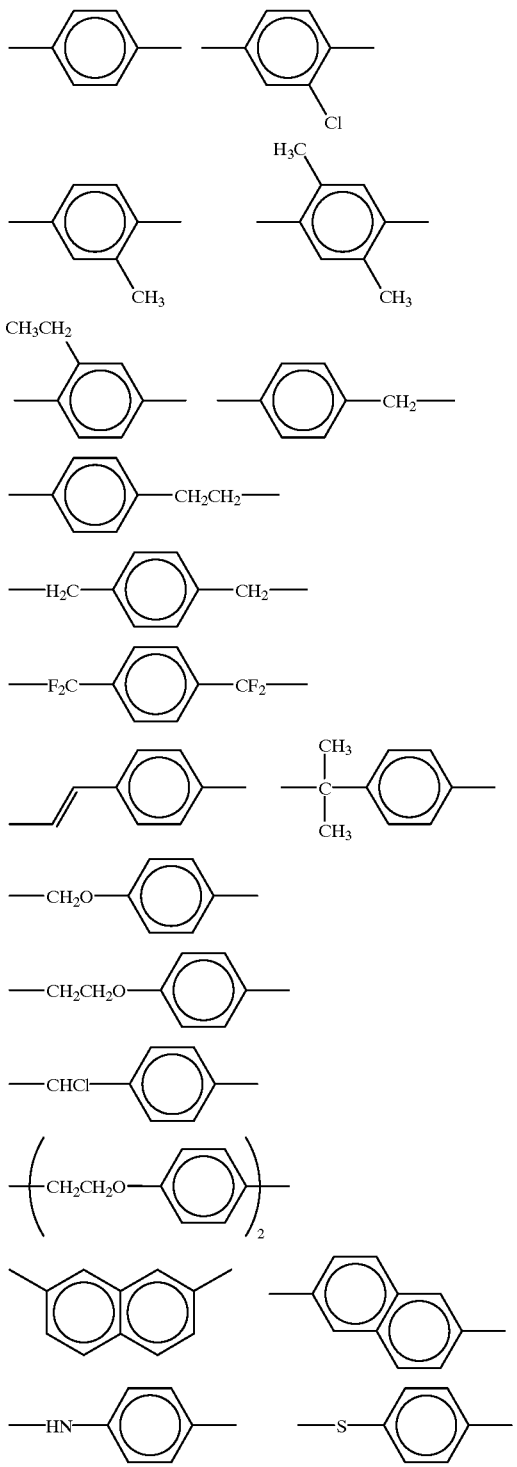

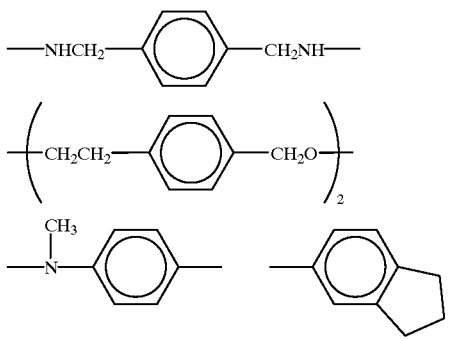

and the like.

Still more generally, the invention provides compounds according to the formula III:

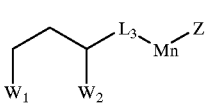

III

In formula III,
- $W^1$, $W^2$ (i) jointly denote —S—S—, —S(O)—S— or —S—S(O)—, or (ii) individually denote a group including an oxidized sulfur atom,
- $L^3$ denotes (i) a single bond, (ii) a methylene group or a $C_{6-10}$ arylene group which is unsubstituted or substituted with a halogen, hydroxyl, amine or unbranched or branched $C_{3-16}$ alkyl, alkenyl or alkynyl group or (iii) a linking group having a Carbon backbone that includes 2 to 16 carbon atoms, wherein a carbon atom in said carbon backbone can be replaced by an oxygen atom. an unsubstituted or substituted amine group, a sulfur atom, an unsubstituted or substituted $C_{6-10}$ aryl group or a combination thereof,
- Y denotes an ester, thioester, urethane or unsubstituted or substituted amide linkage,
- n denotes 0 or 1, and
- Z denotes a group that is in equilibrium at physiological pH with a protonated form thereof and increases the intracellular retention time of said compound with respect to the analogous compound having a carboxyl group, or a pharmaceutically acceptable salt thereof. Both the R and the S enantiomers are provided.

As with the A group in formula II, in formula III the Z group can include additional L and Y groups. Compounds according to formula III also include those in which n=0 (no Y linkage) and $L^3$ is a single bond. In these compounds, the Z group is bonded directly to the dithiolane ring. Exemplary Z groups include imines and guanidines, as well as groups of the formula —$NR^3R^4$.

Compounds according to formula III in which $W^1$ and $W^2$ jointly denote —S—S— are typically non-metabolized forms. The present invention also contemplates and encompasses metabolites of such compounds, in particular, metabolites in which one or both sulfur atoms are oxidized. Such compounds include those compounds of formula III in which $W^1$ and $W^2$ jointly denote —S(O)—S— or —S—S(O)— (thiolsulfinates), or individually denote a group including an oxidized sulfur atom, such as an $SO_3H$ group.

Methods for making the inventive compounds are also provided. In a first method, a compound having the formula I includes the step of reacting a compound having the formula IV

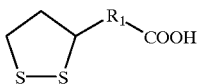   IV with a compound having the formula V $R^6—R^2—NR^3R^4$   V wherein $R^6$ denotes OH, SH, $NH_2$ or $NHR^5$.

Exemplary reagents within the scope of formula IV include lipoic acid ($R^1$=—$(CH_2)_4$—).

Exemplary reagents within the scope of formula V include: ethylenediamine; N,N-dimethylethylenediamine; N,N-dimethylethanolamine; tetramethylenediamine; hexamethylenediamine; 1-pyridylethyleneamine; 1-imidazolyltetramethyleneamine: and the like.

In the inventive method, the reagents are preferably employed in a ratio from about 1:1 to about 1:3 (formula IV: formula V).

In another embodiment, a method of making a compound having the formula II includes the step of reacting a compound having the formula VI

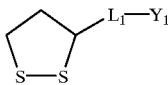   VI with a compound having the formula VII $Y^2—L^2—A$   VII wherein $Y^1$ and $Y^2$ denote groups which react to form an ester, thioester, urethane or unsubstituted or substituted amide linkage.

Exemplary combinations of $Y^1$ and $Y^2$ include —COOH/—$NH_2$; —COOH/—$NHCH_3$; —COOH/—OH; —COOH/—SH; —OH/—NCO; —OC(O)Cl/—$NH_2$; and the like. In the foregoing, either $Y^1$ or $Y^2$ can be the first element of the combination with the remaining group being the second element.

In a further embodiment, a method of making a compound having the formula III includes the step of reacting a compound having the formula VI

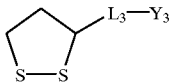   VI with a compound having the formula VIII $Y^4$   VIII to form a product, wherein $Y^3$ denotes $Y^1$ or a group that reacts with $Y^4$ to form an imine or guanidine group, $Y^4$ denotes $Y^2$–Z or a reagent that reacts with Y to form an imine or guanidine group, and $Y^1$ and $Y^2$ denote groups which react to form an ester, thioester, urethane or unsubstituted or substituted amide linkage, and then optionally oxidizing the product.

Exemplary reactions according to the foregoing method include the following: formation of imines ($L^3$=a single bond), with $Y^3$ an aldehyde or ketone group having the formula —C(O)—$R^7$ and $Y^4$ an amine having the formula $H_2N$—$R^8$; formation of imines ($L^3$=a single bond), with $Y^3$ an aldehyde or ketone having the formula $C(O)R^7R^8$ and $Y^4$ an —$NH_2$ group: formation of guanidines ($L^3$=a single boned), with $Y^3$ an alkylisouronium group having the formula

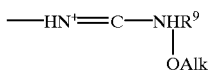

(Alk denoting an alkyl group, preferably a $C_{2-4}$ n-alkyl group) and $Y^4$ an amine having the formula $R^{10}$—$NH_2$. Such reactions result in formation of imine and guanidine groups Z.

Useful solvents for carrying out the reactions according to the invention include dichloromethane (DCM), chloroform, acetonitrile, tetrahydrofuran (THF), N,N-dimethylformamide (DMF) and other non-protonated solvents.

Useful coupling reagents for esterification include thionyl chloride, oxalyl chloride, phosphorus trichloride ($PCl_3$), and dicyclohexylcarbodiimide (DCC). The reactions are advantageously carried out at mild reflux temperature.

For amidation, useful coupling agents include DCC, 1-hydroxybenzotriazole (HOBT), N-hydroxysuccinimide (NHS), benzotriazol-1-yloxy-tris(dimethylamino)phosphonium hexafluorophosphate (BOP), and the like; Amidation can also be carried out by forming the acyl chloride from the acid and reacting it with the appropriate amine in the presence of an excess of the amine or in the presence of another tertiary amine. The reaction can also be carried out by heating the amine and the acid. For amidation reactions, the reaction mixture preferably is stirred overnight at room temperature.

The inventive compounds advantageously are further purified by recrystallization from solvents such as acetone or diethyl ether at low temperatures (e.g., about –20° C. to 4° C.).

Pharmaceutical compositions including the inventive compounds are also provided. The preparation of the pharmaceutical compositions of the invention is carried out in known manner.

Useful carriers and auxiliaries for the inventive compositions include gelatin, natural sugars such as raw sugar or lactose, lecithin, pectin, starches (e.g., corn starch or amylose), cyclodextrins and cyclodextrin derivatives, dextran, polyvinyl pyrrolidone, polyvinyl acetate, gum arabic, alginic acid, tylose, talcum, lycopodium, silica gel (e.g., colloidal silica gel), cellulose, cellulose derivatives such as cellulose ethers (e.g., HPMC), $C_{12-22}$ fatty acids and magnesium, calcium or aluminum salts thereof (e.g., stearates), emulsifiers, oils and fats, in particular vegetable (e.g., peanut oil, castor oil, olive oil, sesame oil, cottonseed oil, corn oil, wheat germ oil, sunflower seed oil, cod liver oil), glycerol esters and partial or complete polyglycerol esters of saturated fatty acids, pharmaceutically acceptably mono- or multivalent alcohols and polyglycols (e.g., polyethylene glycol and derivatives thereof), esters of $C_{2-22}$ aliphatic saturated or unsaturated fatty acids (preferably $C_{10-18}$ acids) with monovalent $C_{1-20}$ aliphatic alcohols or multivalent alcohols such as glycols, glycerol, diethylene glycol, pentaerythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_{1-12}$ alcohols, dimethylacetamide, lactamides, lactates, ethylcarbonales, silicones (e.g., medium-viscosity polydimethyl siloxanes), calcium carbonate, sodium carbonate, calcium phosphate, sodium phosphate, magnesium carbonate, etc.

Additional useful additives include disintegrants, such as cross-linked polyvinyl pyrrolidone, sodium carboxymethyl starch, sodium carboxymethyl cellulose or microcrystalline cellulose.

The inventive compositions can be coated with conventional coating materials such as polymers and copolymers of acrylic acid and/or methacrylic acid and/or their esters (e.g., Eudragit® copolymers), polyvinyl acetate, fats, oils, waxes, fatty alcohols, hydroxypropyl methyl cellulose phthalate or -acetate succinate, cellulose acetate phthalate, starch acetate phthalate, polyvinyl acetate phthalate, carboxy methyl cellulose, methyl cellulose phthalate, methyl cellulose succinate, zein, ethyl cellulose, ethyl cellulose succinate, shellac, gluten, ethylcarboxyethyl cellulose, ethacrylate-maleic acid anhydride copolymer, maleic acid anhydride-vinyl methyl ether copolymer, styrol-maleic acid copolymerizate, 2-ethyl-hexyl-acrylate maleic acid anhydride, crotonic acid-vinyl acetate copolymer, glutaminic acid/glutamic acid ester copolymer, carboxymethylethylcellulose glycerol monooctanoate, cellulose acetate succinate, and polyarginin.

Useful plasticizing agents that can be used as coating materials include citric and tartaric acid esters (acetyltriethyl citrate, acetyl tributyl-, tributyl-, triethyl-citrate), glycerol and glycerol esters (glycerol diacetate, -triacetate, acetylated monoglycerides, castor oil), phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate, benzophenone; diethyl- and dibutylsebacate, dibutylsuccinate, dibutyltartrate, diethylene glycol dipropionate, ethyleneglycol diacetate, -dibutyrate, -dipropionate, tributyl phosphate, tributyrin, polyethylene glycol sorbitan monooleate (polysorbates such as Polysorbat 80), and sorbitan monooleate.

When the inventive compositions are solutions or suspensions, it is useful to employ solvents such as water or physiologically acceptable organic solvents including alcohols such as ethanol, propanol, isopropanol, 1,2-propylene glycol, polyglycols and their derivatives, fatty alcohols, partial esters of glycerol, oils such as peanut oil, olive oil, sesame oil, almond oil, sunflower oil, soya bean oil, castor oil, bovine hoof oil, paraffins, dimethyl sulphoxide, triglycerides and the like.

Injectable solutions or suspensions including the inventive compounds can be prepared using non-toxic parenterally acceptable diluting agents or solvents, such as water, 1,3-butanediol, ethanol, 1,2-propylene glycol, polyglycols mixed with water, glycerol, Ringer's solution, isotonic salt solution or also hardened oils including synthetic mono- or diglycerides or fatty acids such as oleic acid.

Solubilizers and emulsifiers useful in preparing compositions according to the invention include polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols and fatty acids.

For aqueous injection and drinkable solutions, the following stabilizers and solubilizers can be advantageously employed: $C_{2-4}$ aliphatic mono- and multivalent alcohols such as ethanol, n-propanol and glycerol, polyethylene glycols with molecular weights between 200–600, diethylene glycol monoethyl ether, 1,2-propylene glycol, organic amides (e.g., amides of aliphatic $C_{1-6}$ carboxylic acids with ammonia or primary, secondary or tertiary $C_{1-4}$ amines or $C_{1-4}$ hydroxy amines such as urea, urethane, acetamide, N-methyl acetamide, N,N-diethyl acetamide, N,N-dimethyl acetamide, $C_{2-6}$ aliphatic amines and diamines such as ethylene diamine, hydroxyethyl theophylline, tromethamine (e.g., as 0.1 to 20% aqueous solution), and aliphatic amino acids.

Preservatives, stabilizers, buffer substances, flavor correcting agents, sweeteners, colorants and antioxidants can also be employed. Antioxidants can be employed as preservatives, but at higher concentrations antioxidants may serve as co-active ingredients with the inventive compounds (i.e., synergistic activity may occur).

Useful antioxidants include sodium sulphite, sodium hydrogen sulphite, sodium metabisulphite, selenium, inorganic and organic selenium compounds and salts such as sodium selenite, ascorbic acid, ascorbyl palmitate, myristate and stearate, gallic acid, gallic acid alkyl ester, butylhydroxyanisol, nordihydroguaiacic acid and tocopherols, as well as synergists (substances which bind heavy metals through complex formation, for example lecithin, ascorbic acid, phosphoric acid ethylene diamine texraacetic acid, citrates, tartrates). Compositions including selenium salts such as sodium selenite have proven particularly beneficial.

Preservatives useful in the inventive compositions include, for example, sorbic acid, p-hydroxybenzoic acid esters, benzoic acid, sodium benzoate, trichloroisobutyl alcohol, phenol, cresol, benzethonium chloride, chlorhexidine and formalin derivatives.

The pharmaceutical compositions may be applied to the skin or mucous membranes or to the inside of the body, application for example being oral, enteral, pulmonal, nasal, lingual, intravenous, intra-arterial, intracardial, intramuscular, intraperitoneal, intracutaneous, subcutaneous and transdermal.

The inventive compounds can also be formulated as cosmetic preparations, such as lotions, sun screens, ointments, solutions, creams, liposomes and emulsions. Conventional cosmetic additives, carriers, etc. can be combined with the inventive compounds to produce the desired cosmetic preparations in accordance with methods known to those skilled in the art.

The compounds of the present invention are more potent than lipoic acid in preventing expression of adhesion molecules on the membrane surface of endothelial cells, in increasing glucose uptake in rat muscle cells,. and in protecting cells against reactive oxygen species and apoptosis (programmed cell death). The inventive compounds are useful in treating a variety of conditions that involve reactive oxygen species, redox mechanisms and reactive nitrogen species, including without limitation pathological conditions such as exercise-induced tissue damage and physical performance, diabetes (type I and type II), atherosclerosis, an autoimmune disease, a degenerative brain disorder such as Alzheimer's Disease, Parkinson's Disease, Huntington's Disease, epilepsy, a neoplastic disease including cancer, trauma resulting from injuries such as head injuries, ischemic and reperfusion injuries (e.g., cerebral stroke), hepatic disorders such as hepatic biliary cirrhosis, or AIDS, as well as clinical conditions in which apoptosis or necrosis are implicated in pathogenesis. Other conditions which are beneficially treated by the inventive compounds include muscle wasting (cachexia) in cancer and AIDS. The inventive compounds are also beneficially employed in slowing the aging process by combating the intrinsic oxidations that cause injury throughout life.

Tablet and capsule compositions of the invention advantageously include up to about 1000 mg of the inventive compound. Emulsions and liposomes advantageously include up to about 10% (w/v) of the inventive compound. Micellar solutions beneficially contain up to about 25 wt % (w/v) of the inventive compound. Combinations of two or more of the inventive compounds can also be employed in the inventive compositions.

The exact dosage used will vary depending on the particular compound of the invention selected, the age, size, and health of the subject, and the nature and severity of the condition to be treated. However, the appropriate dosage may be determined by one of ordinary skill by routine experimentation, following the guidance set forth herein. As a general guideline, a compound of the invention may be administered daily in a dose of up to about 25 mg/Kg body weight (or about 1.5 g for a 70 Kg subject) as a dietary supplement for prophylaxis from diseases due to oxidative stress. One may administer up to about 50 mg/Kg (or about 3 g) per day for treatment of acute oxidative stress. Suitable subjects include, without limitation, mammals, such as humans, horses, cattle, swine, dogs, cats, and the like, and cells in culture, including mammalian cells, yeast, bacterial cells and the like.

The present invention is illustrated by the following non-limiting examples.

EXAMPLE 1

Syntheses of N,N-Dimethyl-N-2-Amidoethyl Lipoate (HCl) ("LA-PLUS")

One (1) equivalent of lipoic acid was dissolved in 100 ml anhydrous dichloromethane (DCM). Three equivalents of N,N-dimethylethylendiamine were then added, and the mixture was stirred for 5 min. Next, 1.2 equivalents of N-hydroxysuccinimide, dissolved in 5 ml acetonitrile, were added, followed by 1.2 equivalents of dicyclohexylcarbodiimide (DCC) dissolved in 5 mL DCM. The mixture was kept at room temperature overnight under stirring. Then the reaction mixture was transferred into a separatory funnel. The compound was extracted into the aqueous phase by adding concentrated HCl up to acidified pH, and then was extracted back to a 100 ml portion of chloroform using 1N NaOH solution. The organic layer was separated from the aqueous layer and dried with anhydrous magnesium sulfate, filtered and evaporated to dryness.

The compound was then re-dissolved in dichloromethane. HCl gas was bubbled into the organic solvent up to satura-tion. The DCM was evaporated and the HCl salt of N,N-Dimethy,N-2-Amidoethyl Lipoate (LA-PLUS) was precipitated by using anhydrous ether. Yield 80%.

The following tests were conducted using LA and LA-PLUS:

Glutamate Cytotoxicity: Cell Culture

HT4 cells (mouse hippocampal cell line) were purchased from American Type Culture Collection (ATCC, Bethesda, Md.). All experiments reported here were carried out with 10 mM glutamate.

HT4 cells were grown in DMEM supplemented with 10% serum and 100 U/ml penicillin-streptomycin at 37° C. in a humidified atmosphere containing 95% air/5% $CO_2$.

All experiments were performed under the following protocol. Cells were allowed to grow to confluency, were trypsinized and subcultured in culture dishes at a concentration of 375,000 cells per millititer. The cells were continually cultured at 37° C. and were allowed to grow for 24 h, and then were exposed to glutamate treatment.

Determination of Cell Viability

Cell viability was assayed using lactate dehydrogenase (LDH) leakage. After completion of the experiments, culture medium was removed from plates and centrifuged (500 g×5 min) The cells that detached from the monolayer following glutamate treatment were separated by centrifugation of the growth medium. The supernatant medium was mixed with an equal volume of bovine serum albumin (BSA) solution (5% in PBS) to help stabilize LDH activity in the solution saved for storage at 4° C. The pelleted detached cells were washed once with PBS and treated with a lysis buffer (Triton X-100 0.5% v/v in PBS). The resulting lysate was mixed with an equal volume of the BSA solution for storage at 4° C. Attached cells were washed with PBS, treated with the lysis buffer with BSA solution as described above for detached cells. LDH activity was measured from the samples spectrophotometrically within two days of storage. Cell viability was determined using the following formula: viability=attached cell LDH activity/total LDH activity (medium+detached cell LDH activity+attached cell LDH activity).

Flow Cytometric Assay of Fragmented DNA

HT4 cells were exposed to 10 mM glutamate for 24 h with and without antioxidants. Following the treatment the cells were trypsinized, centrifuged, and the pellet was resuspended in a solution containing propidium iodide (50 µg/ml), sodium citrate (0.1%) and Triton-X 100 (0.1%). The permeablized cells were kept in the dark for 6 h at 4° C. and their DNA integrity was analyzed using a flow cytometer (XL, Coulter, FL) with argon-ion laser (excitation 488 nm) and the 575 nm emission was recorded in fluorescence channel 1 (FL1). Data were collected from 40,000 cells. The ratio of fragmented/intact DNA represent the measure of apoptosis. Enzymatic reduction of LA and LA-PLUS by lipoylamide degydrogenase A reaction mixture was prepared including 0.1 mM of NADH, 0.1 U/ml of the enzyme and 0.3 mM of LA or LA-PLUS at room temperature. The conversion rate of LA to DHLA or LA-PLUS to DHLA-PLUS (the reduced form of LA-PLUS, analogous to DHLA) was measured by following the oxidation rate of NADH spectrophotometrically at 340 nm.

Assay for Cells Ability to Retain the Reduced Forms of LA or LA-PLUS

Jurkat T cells or neuronal HT4 cells were incubated with LA (0.1 mM) or LA-PLUS (0.1 mM). The medium of the cells was replaced by phosphate buffer saline that contained 250 uM of 5,5'-dithiobis-(2-nitrobenzoic acid) (DTNB). The free thiols in the medium were trapped by the DTNB and absorption was measured at 420 nm at different time intervals.

Adhesion Molecules Expression

Cells and Cell Culture

EV304 (ECV), a spontaneously transformed immortal human endothelial cell line established from the vein of an apparently normal human umbilical cord, were obtained from ATCC (Bethesda, Md.). ECV cells were grown in medium 199 supplemented with 10% fetal calf serum, 100 U/ml penicillin and 100 μg/ml streptomycin. Cells were maintained in a standard culture incubator with humidified air containing 5% CO2 at 37° C.

Expression of Adhesion Molecules

ECV monolayers were pretreated with LA or LA-PLUS for the time period indicated in the respective figure legend. Following the pretreatment, cells were activated using 20 nM PMA for 24 h. To study ICAM-1 expression, cells were incubated with fluorescein isothiocyanate (FITC) coupled to ICAM monoclonal antibody (Immunotech, Cedex, France) for 30 min at 4° C. Cells were washed twice in Dulbecco's PBS, pH 7.4 (DPBS) and finally resuspended in fresh D-PBS. Expression of ICAM-1 was immediately assayed with a flow cytometer as described in the following section. Appropriate isotypic controls were used for background fluorescence in the ICAM-1 assay.

The fluorescence and light scattering properties (forward scatter FS; side scatter, SS) of the cells were determined by using an EPICS-Elite (Coulter, Miami, Fla.) flow cytometer. Cells with FITC-conjugated antibodies were excited using a 488 nm argon ion laser and emission of FTIC was recorded at 525 nm. In each sample, at least 10,000 gated viable cells were examined. A logarithmic scale was used to measure both background and endothelial cell fluorescence. Background fluorescence was then subtracted from endothelial cell fluorescence, allowing linear comparisons of ICAM-1 expression between various samples.

Glucose Uptake by L6 Rat Muscle Derived Cells

L6 cells were obtained from American Type Culture Collection (MD). Dulbecco's Phosphate Buffered Saline (DPBS) and Dulbecco's Modified Eagle Medium (DMEM) supplemented with high glucose, L-glutamine, pyridoxine hydrochloride and 110 mg/l sodium pyruvate were obtained from GIBCO BRL (Life Technologies, NY). Fetal calf serum (FCS) and other reagents for the culture medium were obtained from the cell culture facility of the University of California-San Francisco. Cell culture.

Undifferentiated mononucleated cells (myoblasts) were used in this study. For experiments, cells were seeded at a concentration of $0.2 \times 10^6$ cells per well in 6-well flat bottom tissue culture treated polystyrene plates (FALCON, Becton Dickinson Labware, NJ). Cultures were grown in DMEM supplemented with 10% FCS, 5 mM glutamine, 0.3% D-glucose, 50 U/ml of penicillin, and 50 mg/ml of streptomycin, in humidified air containing 5% $CO_2$ at 37° C. Cell viability was greater than 97% as estimated by trypan blue exclusion or propidium iodide staining. The cells were split once every third day. All experiments were carried out on cells (6th to 12th passage) in the third day of the last passage.

Cells seeded in 6-well plates were washed thrice with 1 ml transport buffer (140 mM NaCl, 5 mM KCl, 2.5 mM $MgCl_2$, 1 mM $CaCl_2$ in 20 mN tris-HEPES, pH 7.4) at room temperature. Following washing, 1 ml of fresh transport buffer was added to the monolayers, at room temperature. LA or LA PC were added to the cells. Cytochalasin B (final concentration: 20 μM) was added to the specific wells to determine the non-specific binding of [$^{14}$C(U)]-deoxy-D-glucose (DG) to the cells. The [$^{14}$C(U)]-DG was added to the cells for the uptake experiments following 1 h of, LA or LA-PLUS treatments. The uptake of [$^{14}$C(U)]-DG was carried out for 10 min. The reaction was stopped by adding 3 ml of ice-cold transfer buffer to each well using a dispenser. Each well was washed thrice with ice-cold transport buffer followed by lysis of the cells using 0.5 ml of 10% SDS. Radioactivity in each sample was read using a scintillation counter.

Results

To evaluate whether glutamate treatment induced apoptosis in the HT4 cells or facilitated cell death by a necrosis mechanism, the cells were treated for 24 hours with glutamate. The pathway of cell death was explored by staining the cells for 6 h following the glutamate treatment with a DNA-binding fluorescent dye, probidum iodide (PI) in cells permeabilised with a low concentration of detergent (Triton X-100 0.1% w/v). The dye which penetrated to the permeabelized cells stained the nuclear DNA. The cells were analyzed by flow cytometry.

Results showed glutamate-induced cell shrinkage and DNA fragmentation—two characteristic features of apoptosis. In the presence of 50 μM of LA-PLUS the apoptotic process was completely blocked. The anti-apoptotic effect of LA-PLUS in this model was much more pronounced compared to the effect of LA (FIG. 1).

The viability of cells following glutamate treatment was checked in the presence or absence of LA and LA-PLUS. LA-PLUS was found to be more efficient in protecting the HT4 cells than lipoic acid, 50 μM of LA-PLUS were sufficient to completely protect the cells against glutamate cytotoxicity, while LA even at 100 μM did not provide total protection (FIG. 2).

Expression of the adhesion molecule ICAM-1 was induced in human endothelial ECV cells by phorbol ester (phorbol myristate acetate, PMA). PMA induced ICAM-1 expression in the cells was much more effectively down-regulated by LA-PLUS compared to LA when compared for the same concentration used. (FIG. 3)

Stimulation of glucose uptake by L6 myoblasts was studied in response to pretreatment of the cells with LA or LA-PLUS for 1 h. FIG. 4 shows that LA-PLUS was clearly more effective than LA in enhancing glucose uptake by the muscle derived cells.

In order to check whether LA-PLUS is a biologically active metabolic antioxidant the ability of the most specific enzyme that utilized lipoic acid as a substrate, lipoylamide dehydrogenase, to reduce oxidized LA or LA-PLUS to their reduced forms was tested. The conversion of lipoic acid (LA) to dihydrolipoate (DHLA) or LA-PLUS to DHLA-PLUS by purified lipoylamide dehydrogenase (0.1 U/mL) was followed by monitoring NADH consumption at 340 nm. The enzyme was able to reduce the R-stereoisomer of LA-PLUS 30 times faster than the corresponding form of LA (FIG. 5).

FIG. 8 describes the basic difference in the mechanism of action of LA and LA-PLUS.

The efflux of DHLA and DHLA-PLUS from cells was measured in the medium of cells in culture. The medium was composed of PBS and DTNB. Release of DHLA and DHLA-PLUS from Jurkat T cells (FIG. 6A) and HT4 neuronal cells (FIG. 6B) resulted in production of yellow color (TNB), which was measured spectrophotometrically at 420 nm. The results show that the reduced form of LA is effluxed from the cell faster than DHLA-PLUS, which is retained inside the cells (FIG. 7). An illustration of how LA-PLUS crosses biological barriers such as membranes (also showing retention of DHLA-PLUS inside the cell) is given in FIG. 7.

Three different stereo-isomers of LA-PLUS were prepared in order to evaluate whether the protection against glutamate-induced apoptosis in neuronal cells, and the antioxidant activity of the compound, were stereospecific. The ability of (R)-LA-PLUS, (R)(S)-LA-PLUS, or (S)-LA-PLUS (50 μM) to protect HT4 cells against glutamate-induced apoptosis was measured. All three compounds were found to be effective inhibitors of the apoptotic cascade (FIG. 8).

EXAMPLE 2

Syntheses of N,N-Dimethylaminoethyl Lipoate (HCl) ("LA-PLUS Ester")

One (1) equivalent of lipoic acid was dissolved in 100 ml anhydrous DCM. Two equivalents of N,N-dimethylethanolamine were added to the mixture. Five equivalents of thionyl chloride were added dropwise. The mixture was stirred for 30 min, then refluxed for 2 h. The organic solvent was then removed by reduced pressure evaporation, and the ester was crystallized at −20° C. from diethyl ether.

EXAMPLE 3

Emulson Composition

The following composition is prepared:

| | |
|---|---|
| LA-PLUS | 1 g |
| triglyceride oil | 10 g |
| vitamin E | 1% (w/v) |
| phospholipid emulsifier | 1 g |
| water | to 100 g total |

EXAMPLE 4

Liposome Composition

The following composition is prepared:

| | |
|---|---|
| LA-PLUS | 100 mg |
| dipalmitoylphosphatidyl-choline (DPPC) | 900 mg |
| buffered saline | 10 ml |

EXAMPLE 5

Cream Composition

The following composition is prepared:

| | |
|---|---|
| white pareffin | 30 g |
| vitamin E acetate | 1 g |
| LA-PLUS | 1 g |
| emulsifying wax | 10 g |
| water | to 100 g total |

EXAMPLE 6

Viability of HT-4 Cells Following Exposure to Glutamate

The effects of compositions according to the invention on the viability of HT-4 cell treated with glutamate were determined. Seven HT-4 cell cultures were prepared and treated as follows:

1. Control (no glutamate)
2. Treatment with 10 mM glutamate for 12 hours
3. Treatment with 1 μM sodium selenite for 24 hours, followed by treatment with 10 mM glutamate for 12 hours
4. Treatment with 1 μM sodium selenite for 24 hours, followed by treatment with 10 mM glutamate and 10 μM lipoic acid for 12 hours
5. Treatment with 1 μM sodium selenite for 24 hours, followed by treatment with 10 mM glutamate and 10 μM LA-PLUS for 12 hours
6. Twenty-four hours cell growth without sodium selenite followed by treatment with 10 mM glutamate and 10 μM lipoic acid for 12 hours
7. Twenty-four hours cell growth without sodium selenite followed by treatment with 10 mM glutamate and 10 μM LA-PLUS for 12 hours Results are shown in FIG. 9. Enhanced cell viability was observed in the culture treated with combinations of LA-PLUS and sodium selenite (culture 5), and to a lesser extent, the culture treated with lipoic acid and sodium selenite (culture 4).

What is claimed is:

1. A compound having the formula II:

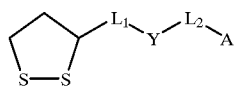

II wherein $L^1$ and $L^2$ independently denote (i) a methylene group or a $C_{6-10}$ arylene group which is unsubstituted or substituted with a halogen, hydroxyl, amine or unbranched or branched $C_{3-16}$ alkyl, alkenyl or alkynyl group or (ii) a linking group having a carbon backbone comprising 2 to 16 carbon atoms, therein a carbon atom in said carbon backbone can be replaced by an oxygen atom, an unsubstituted or substituted amine group, a sulfur atom, an unsubstituted or substituted $C_{6-10}$ aryl group or a combination thereof, Y denotes an ester, thioester, urethane or unsubstituted or alkyl-substituted amide linkage, and A denotes a group containing a nitrogen atom that can be protonated or a pharmaceutically acceptable salt thereof.

2. The compound of claim 1 wherein said compound is in equilibrium with a protonated form thereof at physiological pH.

3. A method of making a compound having the formula II

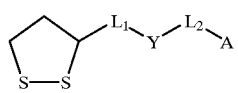

II wherein $L^1$ and $L^2$ independently denote (i) a methylene group or a $C_{6-10}$ arylene group which is unsubstituted or substituted with a halogen, hydroxyl, amine or unbranched or branched $C_{3-16}$ alkyl, alkenyl or alkynyl group or (ii) a linking group having a carbon backbone comprising 2 to 16 carbon atoms, wherein a carbon atom in said carbon backbone can be replaced by an oxygen atom, an unsubstituted or substituted amine group, a sulfur atom, an unsubstituted or substituted $C_{6-10}$ aryl group or a combination thereof, Y denotes an ester, thioester, urethane or unsubstituted or alkyl-substituted amide linkage, and A denotes a group containing a nitrogen atom that is in equilibrium with a protonated form thereof, said method comprising the step of reacting a compound having the formula VI

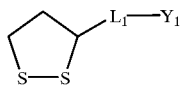

VI with a compound having the formula VII $Y^2$—$L^2$—A VII wherein $Y^1$ and $Y^2$ denote groups which react to form an ester, thioester, urethane or unsubstituted or substituted amide linkage.

4. The method of claim 3 wherein one of said $Y^1$ and $Y^2$ groups is a —COOH group and the other of said $Y^1$ and $Y^2$ groups is selected from the group consisting of —$NH_2$, —$NHR^5$, —OH and —SH, wherein $R^5$ denotes methyl, ethyl, or unbranched or branched $C_{3-16}$ alkyl.

5. A pharmaceutical composition comprising a compound of claim 1 and a pharmaceutically acceptable carrier.

6. The pharmaceutical composition of claim 5 further comprising an additional antioxidant.

7. The pharmaceutical composition of claim 6 wherein said additional antioxidant is sodium selenite.

8. A cosmetic preparation comprising a compound of claim 1 and a cosmetic carrier.

9. A method of treating a condition in a warm-blooded animal that involves a reactive oxygen species or a redox mechanism, said method comprising the step of administering to a warm-blooded animal having said condition an effective amount of a compound of claim 1.

10. The method of claim 9 wherein said condition is a pathological condition selected from the group consisting of exercise-induced tissue damage and physical performance, diabetes, atherosclerosis, an autoimmune disease, a degenerative brain disorder, a neoplastic disease, cerebral ischemia, a hepatic disorder, trauma, cachexia and AIDS.

11. The method of claim 9 wherein said condition is a clinical condition in which apoptosis or necrosis is implicated in pathogenesis.

12. The method of claim 9 wherein said condition is an oxidation process associated with aging.

13. A method of treating a condition in a warm-blooded animal that involves a reactive nitrogen species, said method comprising the step of administering to a warm-blooded animal having said condition an effective amount of a compound of claim 1.

14. A method of reducing the concentration of reactive oxygen species in a living cell, the method comprising administering to the cell an effective amount of compound having the formula II:

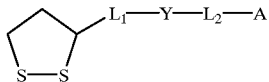

wherein $L_1$ and $L_2$ independently denote (i) a methylene group or a $C_{6-10}$ arylene group which is unsubstituted or substituted with a halogen, hydroxyl, amine or unbranched or branched $C_{3-16}$ alkyl, alkenyl, or alkynyl group or (ii) a linking group having a carbon backbone comprising 2 to 16 carbon atoms, wherein a carbon atom in said carbon backbone can be replaced by an oxygen atom, an unsubstituted or substituted amine group, a sulfur atom, an unsubstituted or substituted $C_{6-10}$ aryl group or a combination thereof, Y denotes an ester, thioester, urethane or unsubstituted or alkyl-substituted amide linkage, and A denotes a group comprising a nitrogen atom that can be protonated, or a pharmaceutically acceptable salt thereof, wherein the administration of the compound reduces the concentration of reactive oxygen species in the cell.

15. A method of inhibiting expression of adhesion molecules on endothelial cell surfaces by administering to endothelial cell surfaces a compound having the formula II:

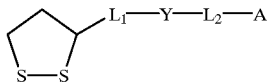

wherein $L_1$ and $L_2$ independently denote (i) a methylene group or a $C_{6-10}$ arylene group which is unsubstituted or substituted with a halogen, hydroxyl, amine or unbranched or branched $C_{3-16}$ alkyl, alkenyl, or alkynyl group or (ii) a linking group having a carbon backbone comprising 2 to 16 carbon atoms, wherein a carbon atom in said carbon backbone can be replaced by an oxygen atom, an unsubstituted or substituted amine group, a sulfur atom, an unsubstituted or substituted $C_{6-10}$ aryl group or a combination thereof;

Y denotes an ester, thioester, urethane or unsubstituted or alkyl-substituted amide linkage, and A denotes a group comprising a nitrogen atom that can be protonated, or a pharmaceutically acceptable salt thereof, wherein the administration of the compound inhibits expression of adhesion molecules on the surfaces of endothelial cells.

* * * * *